(12) United States Patent
Igarashi et al.

(10) Patent No.: US 10,247,698 B2
(45) Date of Patent: Apr. 2, 2019

(54) GAS SENSOR ELEMENT, GAS SENSOR, AND METHOD FOR MANUFACTURING GAS SENSOR ELEMENT

(71) Applicant: NGK SPARK PLUG CO., LTD., Nagoya-shi, Aichi (JP)

(72) Inventors: Ai Igarashi, Konan (JP); Satoshi Okazaki, Kasugai (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 255 days.

(21) Appl. No.: 14/992,577

(22) Filed: Jan. 11, 2016

(65) Prior Publication Data

US 2016/0202207 A1    Jul. 14, 2016

(30) Foreign Application Priority Data

Jan. 13, 2015  (JP) .................................. 2015-004140
Nov. 17, 2015  (JP) .................................. 2015-224340

(51) Int. Cl.
*G01N 27/407* (2006.01)
*G01N 27/417* (2006.01)
(Continued)

(52) U.S. Cl.
CPC ....... *G01N 27/417* (2013.01); *B28B 17/0009* (2013.01); *B28B 19/0015* (2013.01); *G01N 27/4071* (2013.01)

(58) Field of Classification Search
CPC ............. G01N 27/407; G01N 27/4071; G01N 27/406–27/41; G01N 33/0004–33/0075
See application file for complete search history.

(56) References Cited

U.S. PATENT DOCUMENTS

| 5,384,030 A * | 1/1995 | Duce .................. G01N 27/4073 204/400 |
| 2005/0189222 A1* | 9/2005 | Tsuzuki .................. B28B 1/008 204/424 |
| 2013/0032480 A1* | 2/2013 | Ito ........................ G01N 27/406 204/424 |

FOREIGN PATENT DOCUMENTS

CN    1694599 A    11/2005
JP    2010-145214 A    7/2010
(Continued)

OTHER PUBLICATIONS

Suganuma (JP 2010145214 A, machine translation) (Year: 2010).*
(Continued)

*Primary Examiner* — Maris R Kessel
*Assistant Examiner* — Joshua L Allen
(74) *Attorney, Agent, or Firm* — Stites & Harbison, PLLC; Jeffrey A. Haeberlin; James R. Hayne

(57) ABSTRACT

A gas sensor element that includes a composite ceramic layer including a plate-shaped insulating portion which contains an insulating ceramic and has a through-hole, and an electrolyte portion which contains a solid electrolyte ceramic, and a portion disposed in the through-hole where the electrolyte portion is thicker than the insulating portion. A first conductor layer is formed over a first insulating surface of the insulating portion and a first electrolyte surface of the electrolyte portion. The electrolyte portion has an extending portion which is overlaid on the first insulating surface and extends toward the outside of the through-hole. The thickness of the extending portion is decreased toward an outer periphery of the extending portion, and the outer periphery of the extending portion is continuously connected to the first insulating surface. A first extending surface of the extending portion continuously connects the first insulating surface and the first electrolyte surface.

5 Claims, 11 Drawing Sheets

(51) Int. Cl.
*B28B 17/00* (2006.01)
*B28B 19/00* (2006.01)

(56) References Cited

FOREIGN PATENT DOCUMENTS

JP       2010145214 A  *  7/2010
JP         5104744 B2    12/2012

OTHER PUBLICATIONS

The State Intellectual Property Office of P.R. China, Office Action issued in corresponding Application No. 201610021467 dated Apr. 27, 2018. (An English translation is not available.).

\* cited by examiner (a)

(b)

(a)

(b)

(a)

(b)

GAS SENSOR ELEMENT, GAS SENSOR, AND METHOD FOR MANUFACTURING GAS SENSOR ELEMENT

CROSS REFERENCE TO RELATED APPLICATIONS

The present application claims priority to Japanese Patent Application Nos. 2015-004140 and 2015-224340, which were filed on Jan. 13, 2015 and Nov. 17, 2015, respectively, the disclosures of which are herein incorporated by reference in their entirety.

BACKGROUND OF THE INVENTION

Field of the Invention

The present invention relates to a gas sensor element, a gas sensor, and a method for manufacturing the gas sensor element.

Description of Related Art

Gas sensors are used for combustion control of internal combustion engines. A gas sensor includes a gas sensor element that outputs, as a detection signal, the concentration of a specific component (e.g., oxygen) in an exhaust gas from an internal combustion engine. For example, a gas sensor element disclosed in Patent Document 1 includes an alumina sheet having a through-hole penetrating therethrough in the thickness direction, and the through-hole is filled with a zirconia filling portion having oxygen ion conductivity. A pair of electrodes are provided on both surfaces of the zirconia filling portion. Patent Document 1 discloses a structure in which the thickness of the zirconia filling portion is larger than the depth of the through-hole (i.e., the thickness of the alumina sheet) so that the zirconia filling portion projects from the through-hole, and the size of the projected part of the zirconia filling portion is larger than the opening area of the through-hole.

RELATED ART DOCUMENTS

Patent Document 1 is Japanese Laid-Open Patent Publication No. 2010-145214.

BRIEF SUMMARY OF THE INVENTION

Generally, a wiring (conductor layer) for taking an electric signal from the electrode disposed on the zirconia filling portion to the outside is provided on the alumina sheet. However, Patent Document 1 does not indicate that such a wiring is provided. Therefore, when a wiring extending from the electrode on the zirconia filling portion to an end portion of the alumina sheet is to be provided, the structure of the zirconia filling portion disclosed in Patent Document 1 may cause cracking or breaking of the wiring at a corner of the zirconia filling portion projected from the through-hole. Therefore, a technique is desired which is able to suppress occurrence of cracking and breaking in a conductor layer including an electrode and a wiring, in a gas sensor element in which the thickness of an insulating portion having a through-hole is different from the thickness of an electrolyte portion filled in the through-hole.

The present invention has been made to solve the above problems and can be embodied in the following modes.

(1) According to an aspect of the present invention, a gas sensor element is provided. This gas sensor element includes: a composite ceramic layer including a plate-shaped insulating portion which contains (i.e., includes) an insulating ceramic and has (i.e., defines) a through-hole penetrating therethrough in a direction of a thickness of the insulating portion, and an electrolyte portion which contains (i.e., includes) a solid electrolyte ceramic and having at least a portion disposed in the through-hole; and a first conductor layer formed over a first insulating surface as a surface, on one side, of the insulating portion and a first (primary) electrolyte surface as a surface, on the one side, of the electrolyte portion. The thickness of the electrolyte portion is larger than the thickness of the insulating portion. The electrolyte portion has, on the first (primary) electrolyte surface side, an extending portion which is overlaid on (i.e., that overlays) the first insulating surface and extends toward the outside of the through-hole. The thickness of the extending portion decreases toward an outer periphery of the extending portion. The outer periphery of the extending portion is continuously connected to the first insulating surface. A first extending surface as a surface, on the one side, of the extending portion continuously connects (i.e., extends between) the first insulating surface and the first (primary) electrolyte surface. In the gas sensor element according to the above aspect, the electrolyte portion disposed in the through-hole of the insulating portion is provided with the extending portion that is overlaid on the first insulating surface, on the one side, of the insulating portion and extends toward the outside of the through-hole, and the outer periphery of the extending portion is continuously connected to the first insulating surface, and further, the first extending surface as a surface, on the one side, of the extending portion continuously connects the first insulating surface and the first (primary) electrolyte surface. Therefore, it is possible to suppress occurrence of cracking and breaking in the first conductor layer formed over the first insulating surface and the first (primary) electrolyte surface.

(2) In the gas sensor element according to the above aspect, a side end portion, on the first insulating surface side, of the through-hole formed in (i.e., defined by) the insulating portion may have an arc shape that is convex from an inner side toward an outer side in the thickness direction of the insulating portion. According to the gas sensor element of the above aspect, since an angular corner portion is not formed at the portion where the electrolyte portion and the insulating portion are overlaid with each other, on the first insulating surface side of the insulating portion. Therefore, it is possible to alleviate concentration of stress on the boundary between the electrolyte portion and the insulating portion on the first insulating surface side. Thus, it is possible to suppress occurrence of cracking in the extending portion, starting from any point on the boundary between the electrolyte portion and the insulating portion, whereby durability of the gas sensor element can be increased.

The present invention can be embodied in various forms other than the gas sensor element. For example, the present invention can be embodied in forms such as a gas sensor including the gas sensor element, and a method for manufacturing the gas sensor element or the gas sensor.

DETAILED DESCRIPTION OF EXEMPLARY EMBODIMENTS OF THE INVENTION

A. First Embodiment

Figure 1:
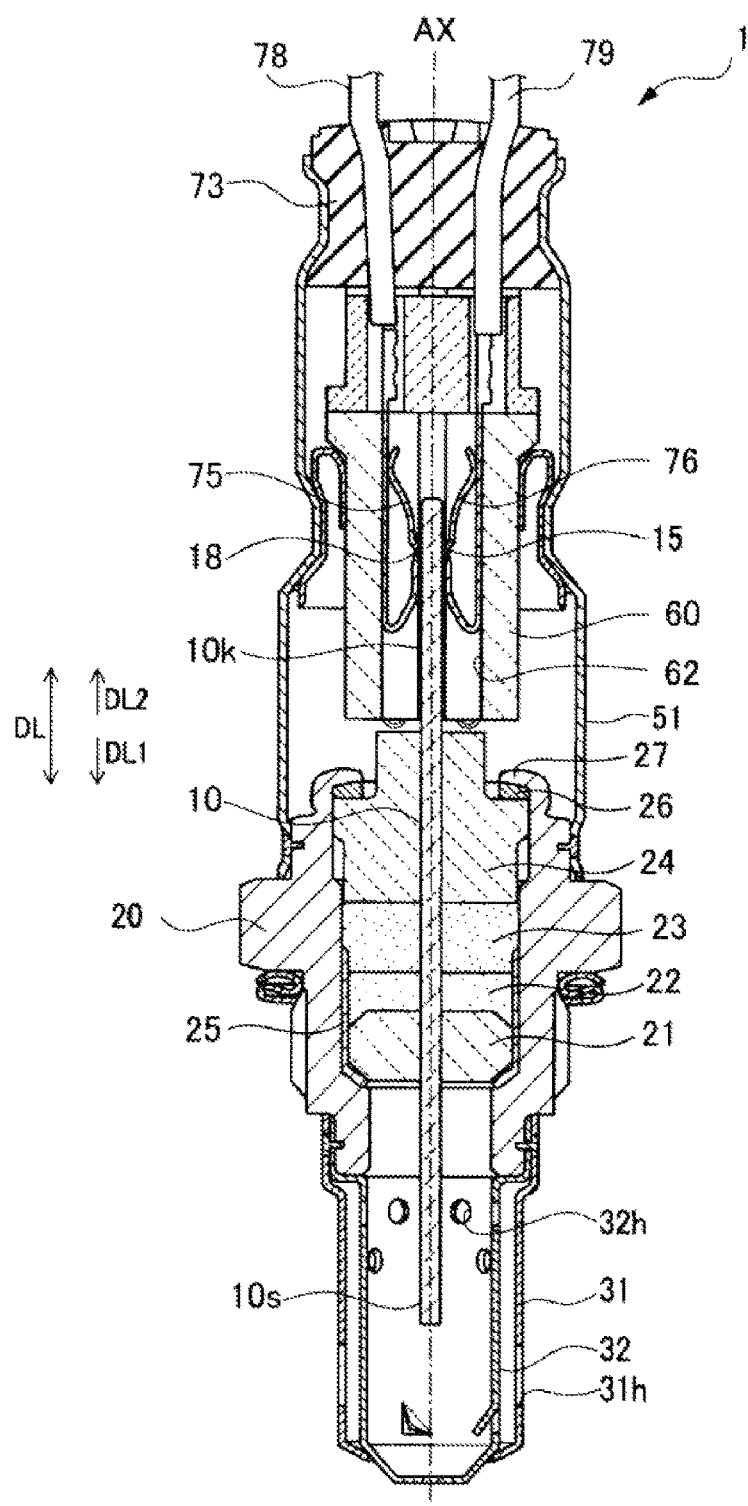
FIG. 1 is a vertical cross-sectional view of a gas sensor cut along an axis thereof.

FIG. 1 is a vertical cross-sectional view of a gas sensor 1 cut along an axis AX, according to a first embodiment of the present invention. The gas sensor 1 is, for example, mounted to an exhaust pipe of an internal combustion engine and used as an oxygen sensor. In the following description, the lower side of the gas sensor 1 shown in FIG. 1 is referred to as a front side DL1 and the upper side thereof is referred to as a rear side DL2.

The gas sensor 1 includes a gas sensor element 10 and a metallic shell 20 as major components. The gas sensor element 10 is a plate-shaped element extending in a longitudinal direction DL, and is configured to be able to detect the concentration of oxygen in an exhaust gas which is a measurement target gas. The gas sensor element 10 is disposed in the gas sensor 1 so that a center line along its own longitudinal direction DL matches the axis AX.

The metallic shell 20 is a tubular metal in which the gas sensor element 10 is held. The metallic shell 20 holds the gas sensor element 10 in such a manner that a front end portion 10s of the gas sensor element 10 protrudes toward the front side relative to the metallic shell 20 and a rear end portion 10k of the gas sensor element 10 protrudes toward the rear side relative to the metallic shell 20. On the front side of the metallic shell 20, an external protector 31 and an internal protector 32 which are made of a metal are disposed so as to cover the front end portion 10s of the gas sensor element 10. The external protector 31 and the internal protector 32 have a plurality of gas introduction holes 31h, 32h. Through the gas introduction holes 31h, 32h, the measurement target gas outside the external protector 31 is introduced to a space around the front end portion 10s of the gas sensor element 10 disposed inside the internal protector 32.

In the metallic shell 20, an annular ceramic holder 21, powder filler layers 22, 23 (hereinafter also referred to as talc rings 22, 23), and a ceramic sleeve 24 are disposed in order from the front side DL1 to the rear side DL2 so as to surround the outer periphery of the sensor element 10. A metal holder 25 is disposed on the outer circumferences of the ceramic holder 21 and the talc ring 22. In addition, a crimping packing 26 is disposed on the rear side of the ceramic sleeve 24. A rear end portion 27 of the metallic shell 20 is crimped via the crimping packing 26 so as to press the ceramic sleeve 24 toward the front side.

On the rear side of the metallic shell 20, a tubular outer casing 51 is disposed to as to surround the rear end portion 10k of the gas sensor element 10. Further, a separator 60 is disposed inside the outer casing 51. The separator 60 surrounds the periphery of the rear end portion 10k of the gas sensor element 10, and separates five terminal members 75, 76 (only two of them are shown in FIG. 1) mounted to the front ends of five lead wires 78, 79 (only two of them are shown in FIG. 1) from each other, and holds the terminal members. The separator 60 has an insertion hole 62 penetrating therethrough in the direction of the axis AX. The rear end portion 10k of the gas sensor element 10 is inserted in the insertion hole 62. In the insertion hole 62, the five terminal members 75, 76 are disposed to be separated from each other, and are elastically in contact with and electrically connected to later-described pad portions 14 to 18 of the gas sensor element 10, respectively. On the rear side of the outer casing 51, a grommet 73 that closes a rear-end opening of the outer casing 51 is fitted. The five lead wires 78, 79 penetrate through the grommet 73.

Figure 2:
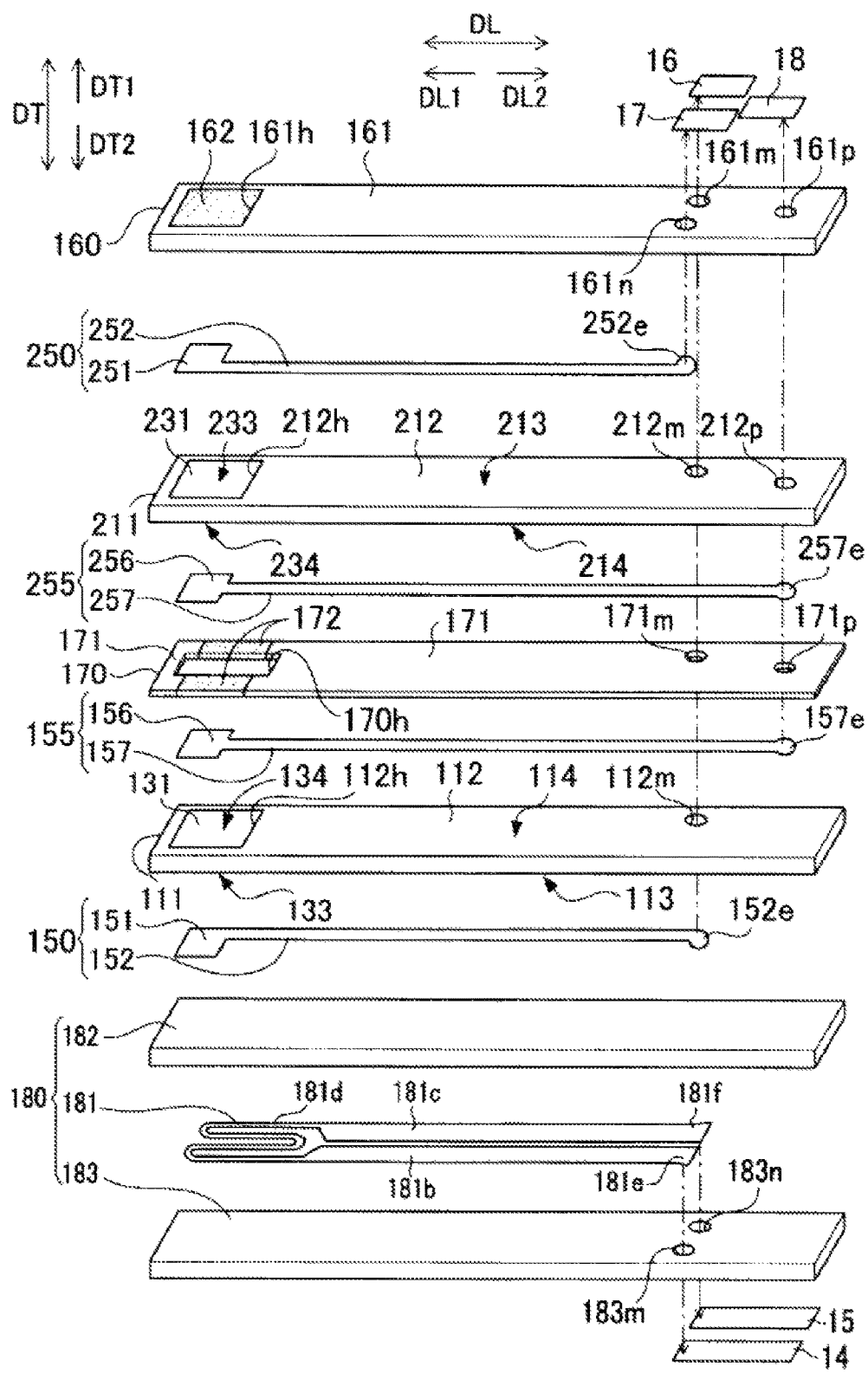
FIG. 2 is an exploded perspective view of a gas sensor element according to a first embodiment.
Figure 3:
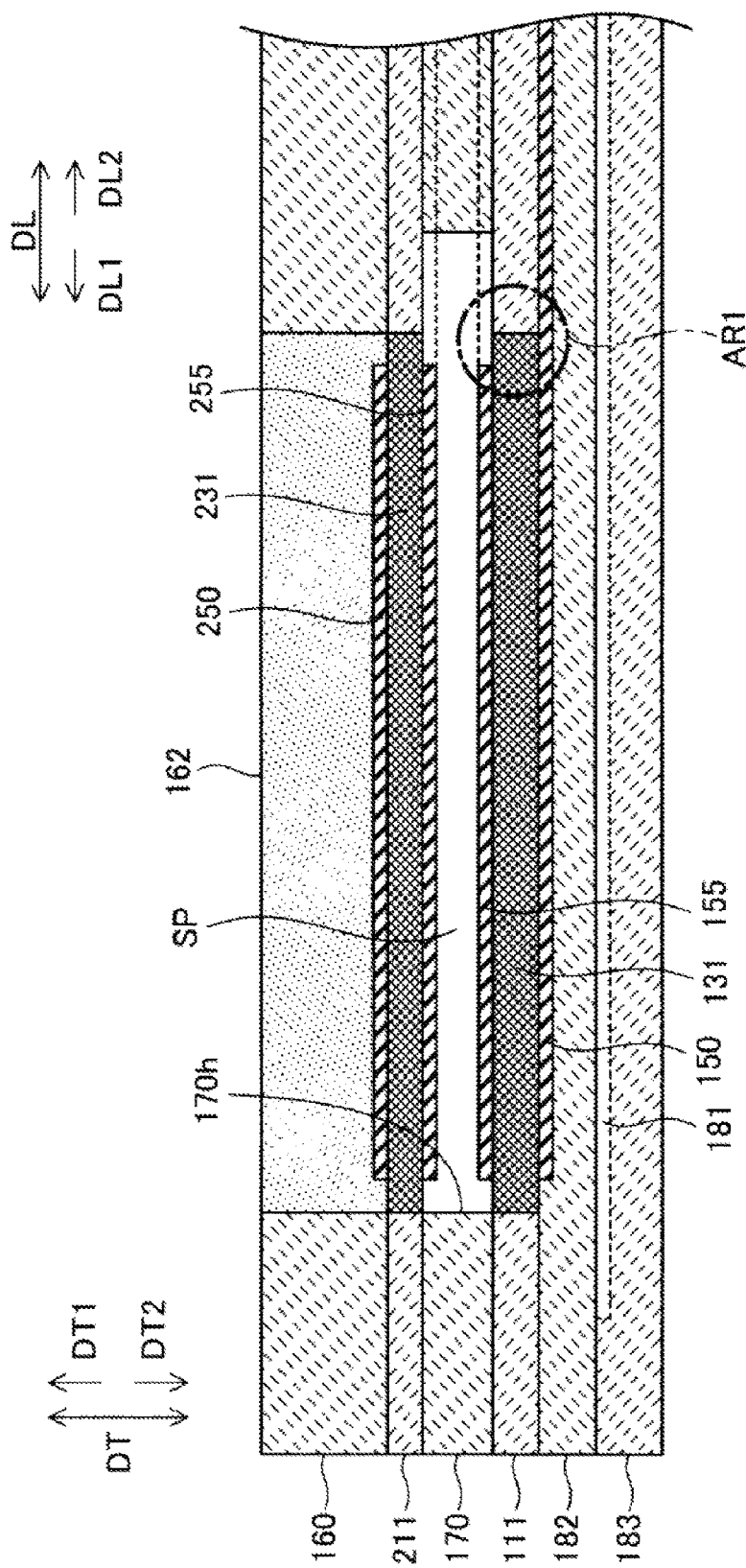
FIG. 3 is a cross-sectional view schematically showing a stacked state of members of the gas sensor element according to the first embodiment.

FIG. 2 is an exploded perspective view of the gas sensor element 10. FIG. 3 is a cross-sectional view schematically showing a stacked state of the members of the gas sensor element 10. In FIG. 2 and FIG. 3, the left side corresponds to the front side DL1 of the gas sensor 1, and the right side corresponds to the rear side DL2 thereof.

The gas sensor element 10 is composed of a plurality of ceramic layers and conductor layers stacked in the thickness direction DT. Specifically, the gas sensor element 10 includes: a detection composite ceramic layer 111 used for detection of the concentration of oxygen in the measurement target gas; and a pump composite ceramic layer 211 that is located on the one side DT1 in the thickness direction relative to the detection composite ceramic layer 111, and is used for adjustment of the concentration of oxygen in the measurement target gas in a measurement chamber SP (refer to FIG. 3). Further, an insulating layer 170 is disposed between the detection composite ceramic layer 111 and the pump composite ceramic layer 211. A first conductor layer 150 and a second conductor layer 155 are formed on the other side DT2 and the one side DT1, in the thickness direction, of the detection composite ceramic layer 111, respectively. A first conductor layer 250 and a second conductor layer 255 are formed on the one side DT1 and the other side DT2 of the pump composite ceramic layer 211, respectively. Further, a heater layer 180 is stacked on the other side DT2 of the detection composite ceramic layer 111 and the first conductor layer 150, and a protection layer 160 is stacked on the one side DT1 of the pump composite ceramic layer 211 and the first conductor layer 250.

The detection composite ceramic layer 111 includes: a detection insulating portion 112 that has a rectangular plate shape, is made of an insulating ceramic (alumina), and has a through-hole 112h that penetrates therethrough in the thickness direction DT and has a rectangular shape in a plan view; and a detection electrolyte portion 131 that has a plate shape, is made of a solid electrolyte (zirconia) ceramic, and is disposed in the through-hole 112h of the detection insulating portion 112. The detection insulating portion 112 includes a first insulating surface 113 facing the other side DT2, and a second insulating surface 114 facing the one side DT1. The detection electrolyte portion 131 includes a first electrolyte surface 133 facing the other side DT2, and a second electrolyte surface 134 facing the one side DT1.

The first conductor layer 150 includes: a rectangular first electrode layer 151 formed on the first electrolyte surface 133 of the detection electrolyte portion 131 so as to be smaller than the opening area of the through-hole 112h; and a strip-shaped first lead layer 152 extending from the first electrode layer 151 to the rear side DL2 in the longitudinal direction. The first lead layer 152 extends from a position on the first electrolyte surface 133 to a position on the first insulating surface 113 across the first electrolyte surface 133 and the first insulating surface 113. Like the first conductor layer 150, the second conductor layer 155 includes: a rectangular second electrode layer 156 formed on the second electrolyte surface 134 of the detection electrolyte portion 131 so as to be smaller than the opening area of the through-hole 112h; and a strip-shaped second lead layer 157 extending from the second electrode layer 156 to the rear side DL2. The second lead layer 157 extends from a position on the second electrolyte surface 134 to a position on the second insulating surface 114 across the second electrolyte surface 134 and the second insulating surface 114.

The pump composite ceramic layer 211 includes: a pump insulating portion 212 that has a rectangular plate shape, is made of an insulating ceramic (alumina), and has a through-hole 212h that penetrates therethrough in the thickness direction DT and has a rectangular shape in a plan view; and a pump electrolyte portion 231 that has a plate shape, is made of a solid electrolyte (zirconia) ceramic, and is disposed in the through-hole 212h of the pump insulating portion 212. The pump insulating portion 212 has a first insulating surface 213 facing the one side DT1 in the thickness direction, and a second insulating surface 214 facing the other side DT2 in the thickness direction. The pump electrolyte portion 231 has a first electrolyte surface 233 facing the one side DT1, and a second electrolyte surface 234 facing the other side DT2.

The first conductor layer 250 includes: a rectangular first electrode layer 251 formed on the first electrolyte surface 233 of the pump electrolyte portion 231 so as to be smaller than the opening area of the through-hole 212h; and a strip-shaped first lead layer 252 extending from the first electrode layer 251 to the rear side DL2. The first lead layer 252 extends from a position on the first electrolyte surface 233 to a position on the first insulating surface 213 across the first electrolyte surface 233 and the first insulating surface 213. Like the first conductor layer 250, the second conductor layer 255 includes: a rectangular second electrode layer 256 formed on the second electrolyte surface 234 of the pump electrolyte portion 231 so as to be smaller than the opening area of the through-hole 212h; and a strip-shaped second lead layer 257 extending from the second electrode layer 256 to the rear side DL2. The second lead layer 257 extends from a position on the second electrolyte surface 234 to a position on the second insulating surface 214 across the second electrolyte surface 234 and the second insulating surface 214.

The insulating layer 170 has a rectangular through-hole 170h that penetrate therethrough so as to overlap the through-holes 112h, 212h. The through-hole 170h is enclosed by the insulating layer 170, the detection composite ceramic layer 111 (the detection electrolyte portion 131), and the pump composite ceramic layer 211 (the pump electrolyte portion 231), thereby forming a hollow measurement chamber SP. The insulating layer 170 is composed of a body portion 171 made of dense alumina, and two porous portions 172. The two porous portions 172 are made of a porous ceramic. The two porous portions 172 form portions of two sides of the through-hole 170h, extending along the longitudinal direction DL, respectively, and are exposed at the lateral sides (in the directions orthogonal to the longitudinal direction DL and the thickness direction DT). Each porous portion 172 is a diffusion rate limiting layer that introduces the measurement target gas from the outside of the gas sensor element 10 into the measurement chamber SP under a predetermined rate-limiting condition.

On the one side DT1, in the thickness direction, of the pump composite ceramic layer 211, the protection layer 160 is stacked so as to cover the first conductor layer 250. The protection layer 160 is composed of a porous portion 162 covering the first electrode layer 251 and the pump electrolyte portion 231, and a protection portion 161. The protection portion 161 is a dense ceramic that has a through-hole 161h penetrating therethrough so as to surround and house the porous portion 162, and is overlaid on the pump insulating portion 212 to protect it.

On the protection portion 161, three sensor pad portions 16, 17 and 18 are formed, with which three terminal members 75 (refer to FIG. 1) are to be in contact. The sensor pad portion 16 electrically communicates with an end portion 152e, on the rear side DL2, of the first conductor layer 150 (the first lead layer 152) via through-holes 161m, 212m, 171m and 112m. The sensor pad portion 17 electrically communicates with an end portion 252e, on the rear side DL2, of the first conductor layer 250 (the first lead layer 252) via the through-hole 161n. Further, the sensor pad portion 18 electrically communicates with an end portion 157e of the second conductor layer 155 (the second lead layer 157) and an end portion 257e of the second conductor layer 255 (the second lead layer 257) via the through-holes 161p, 212p and 171p.

The heater layer 180 includes two plate-shaped insulating layers 182, 183 made of alumina, and a heater pattern 181 embedded therebetween. The heater pattern 181 is composed of a meandering heat generating portion 181d, and a first lead portion 181b and a second lead portion 181c connected to the both ends of the heat generating portion 181d, respectively, and linearly extending. On the other side DT2 of the insulating layer 183, two heater pad portions 14, 15 are formed, with which two terminal members 76 (refer to FIG. 1) are to be in contact. The heater pad portion 14 electrically communicates with an end portion 181e, on the rear side DL2, of the first lead portion 181b via a through-hole 183m. The heater pad portion 15 electrically communicates with an end portion 181f, on the rear side DL2, of the second lead portion 181c via a through-hole 183n.

In the gas sensor element 10 according to the present embodiment, a reference gas is formed in the porous first electrode layer 151 in advance by supplying oxygen thereto. Then, the direction and magnitude of a current that flows between the first electrode layer 251 and the second electrode layer 256 sandwiching the pump electrolyte portion 231 are adjusted by using the three lead wires 78 electrically communicating with the sensor pad portions 16 to 18, in order to pump oxygen from the measurement chamber SP into the porous portion 162 or conversely pump oxygen into the measurement chamber SP by using the pump electrolyte portion 231 so that a potential difference that occurs between the first electrode layer 151 and the second electrode layer 156 sandwiching the detection electrolyte portion 131 has a predetermined value (the oxygen concentration in the measurement chamber SP is constant). Since the magnitude of the current flowing between the first electrode layer 251 and the second electrode layer 256 has a value according to the concentration of oxygen in the measurement target gas that flows into the measurement chamber SP via the porous portion 172, the concentration of oxygen in the measurement target gas can be detected on the basis of the magnitude of the current. When measuring the oxygen concentration, the heater pattern 181 is caused to generate heat by a current supplied thereto via the two lead wires 79 electrically communicating with the heater pad portions 14, 15, whereby the detection electrolyte portion 131 and the pump electrolyte portion 231 are heated and activated.

Figure 4:
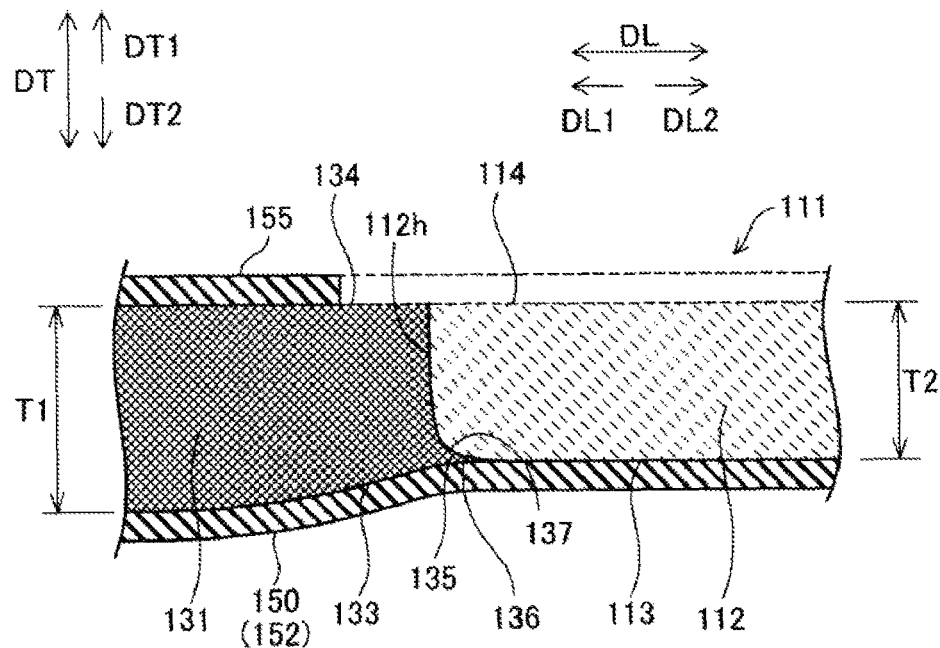
FIG. 4 is an enlarged view of a part around a sectional portion AR1 shown in FIG. 3.

FIG. 4 is an enlarged view of a part of the structure shown in FIG. 3, around a sectional portion AR1. FIG. 4 shows the structure of a part of the detection composite ceramic layer 111 of the gas sensor element 10 according to the present embodiment, around the boundary between the detection electrolyte portion 131 and the detection insulating portion 112. As shown in FIG. 4, in the present embodiment, a thickness T1 of the detection electrolyte portion 131 is larger than a thickness T2 of the detection insulating portion 112. The electrolyte portion 131 protrudes toward the first electrolyte surface 133. In addition, the detection electrolyte portion 131 has, on the first electrolyte surface 133 side, an extending portion 135 that is overlaid on the first insulating surface 113 and extends to the outside of the through-hole 112h. The thickness of the extending portion 135 is decreased toward the outer periphery of the extending portion 135. The outer periphery of the extending portion 135 is continuously connected to the first insulating surface 113. Further, a first extending surface 136, which is a surface of the extending portion 135 on the other side DT2, continuously connects the first insulating surface 113 and the first electrolyte surface 133. Therefore, the first insulating surface 113, the first extending surface 136, and the first electrolyte surface 133 are connected so as to form a single plane having no step difference. In other words, the first extending surface 136 continuously extends between the first insulating surface 113 and the first (primary) electrolyte surface 133. A side end portion 137, on the first insulating surface 113 side, of the through-hole 112h formed in the detection insulating portion 112 has an arc shape that is convex from the inner side to the outer side in the thickness direction of the detection insulating portion 112. That is, the opening area of the through-hole 112h on the first insulating surface 113 side is increased from the inner side toward the outer side in the thickness direction. The structure shown in FIG. 4 is identical over the entire outer periphery of the detection electrolyte portion 131. The thickness T1 of the detection electrolyte portion 131 is the maximum thickness of the detection electrolyte portion 131. Likewise, the thickness T2 of the detection insulating portion 112 is the maximum thickness of the detection insulating portion 112.

Figure 5:
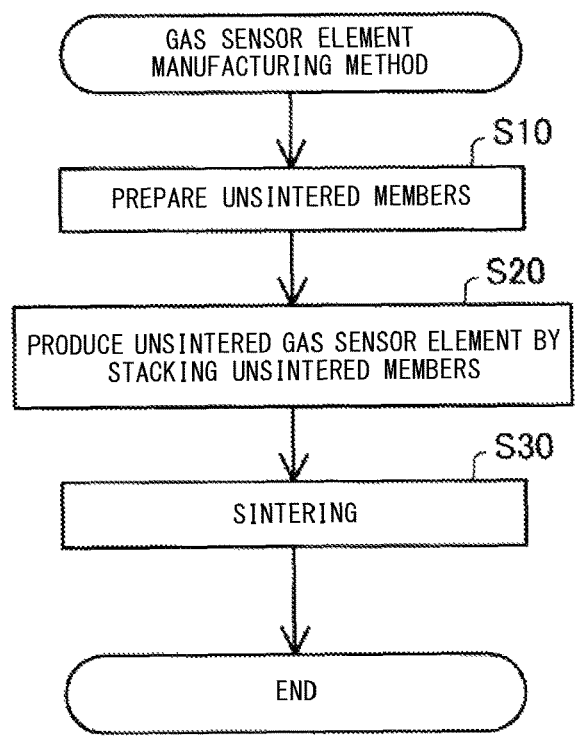
FIG. 5 is a flowchart showing a method for manufacturing the gas sensor element.

FIG. 5 is a flowchart showing a method for manufacturing the gas sensor element 10. Hereinafter, the members that have been sintered and the corresponding unsintered members are denoted by the same reference numerals for convenience of explanation. In the manufacturing method according to the present embodiment, first, an unsintered member is prepared for each of the components of the gas sensor element 10 (step S10). Specifically, an unsintered protection layer 160, an unsintered pump composite ceramic layer 211, an unsintered insulating layer 170, an unsintered detection composite ceramic layer 111, and unsintered insulating layers 182, 183 are prepared. A method for producing the pump composite ceramic layer 211 and the detection composite ceramic layer 111 will be described later.

After the unsintered members have been prepared, the prepared unsintered members are stacked in order as shown in FIG. 2 to produce an unsintered gas sensor element 10 (step S20). In advance of step S20, an unsintered heater pattern 181 is formed by screen printing on the unsintered insulating layer 183 on the one side DT1 or the unsintered insulating layer 182 on the other side DT2.

After the unsintered gas sensor element 10 has been produced in step S20, the unsintered gas sensor element 10 is sintered by a known technique (step S30). Through the above-mentioned steps, the gas sensor element 10 is completed.

Figure 6:
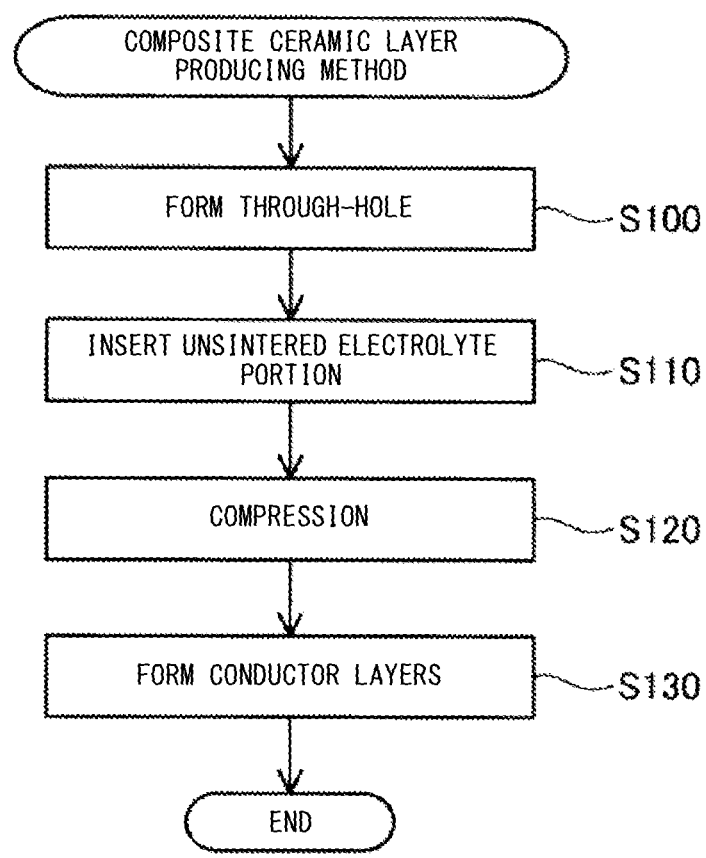
FIG. 6 is a flowchart showing a method for producing a composite ceramic layer.

FIG. 6 is a flowchart showing a method for producing the unsintered detection composite ceramic layer 111 and the unsintered pump composite ceramic layer 211 which are prepared in step S10 of FIG. 5. Since the production method for the unsintered pump composite ceramic layer 211 is identical to that for the unsintered detection composite ceramic layer 111, the production method for the unsintered detection composite ceramic layer 111 will be described while the production method for the unsintered pump composite ceramic layer 211 will be omitted.

First, an unsintered insulating-portion sheet (insulating green sheet) 112s having a thickness of 155±20 μm and an unsintered electrolyte-portion sheet (electrolyte green sheet) 131s having a thickness of 200±20 μm larger than the above thickness, which are formed by a doctor blade method, are prepared in advance. Then, a through-hole 112h is formed in the unsintered insulating-portion sheet 113s (step S100). When the thickness of the unsintered insulating-portion sheet 112s is 155±20 μm and the thickness of the unsintered electrolyte-portion sheet 131s is 200±20 μm, the thickness of the unsintered electrolyte-portion sheet 131s can be made at least 5 μm larger than the thickness of the unsintered insulating-portion sheet 112s.

Figure 7:
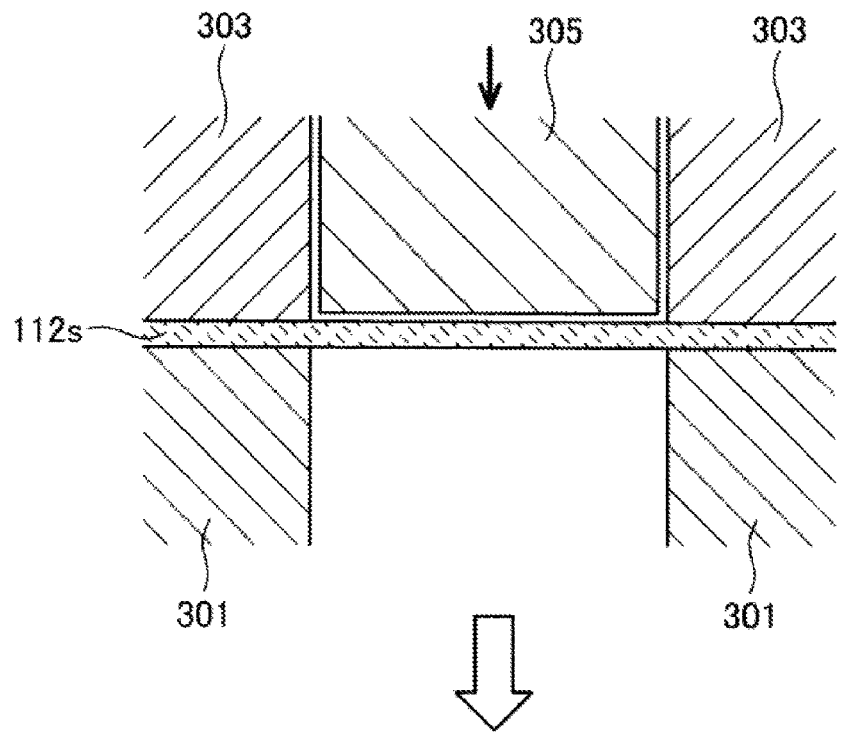
FIG. 7 is a view for explaining a method for forming a through-hole in a sheet for an unsintered insulating portion.
Figure 7:
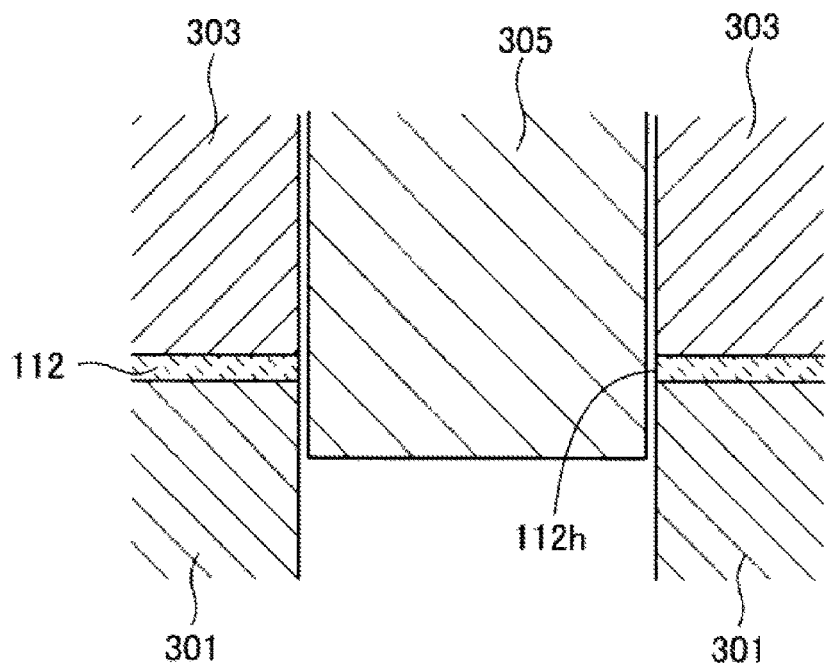
Figure 8:
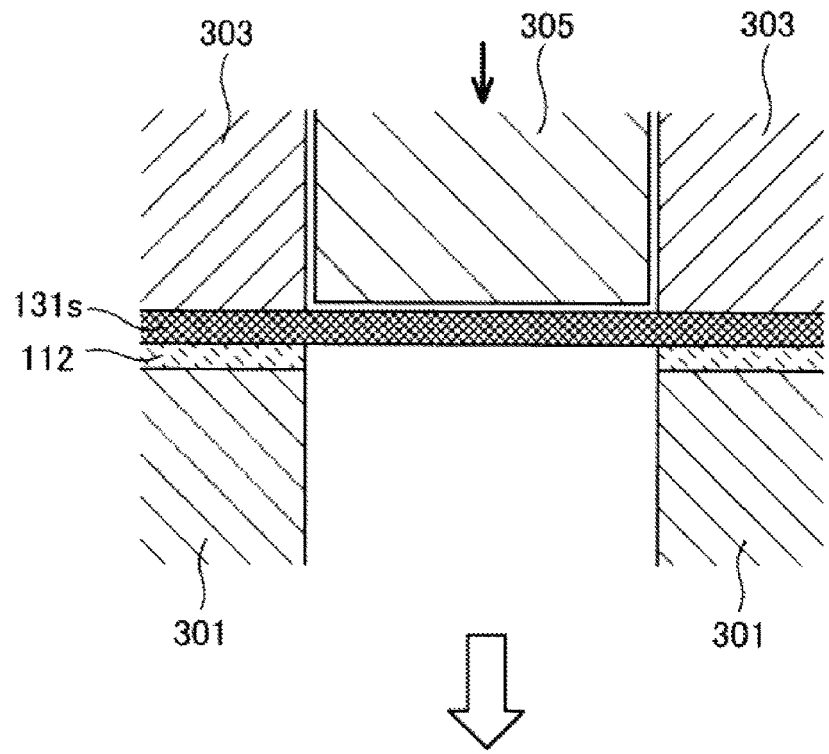
FIG. 8 is a view for explaining a method for inserting an unsintered electrolyte portion into the through-hole.
Figure 8:
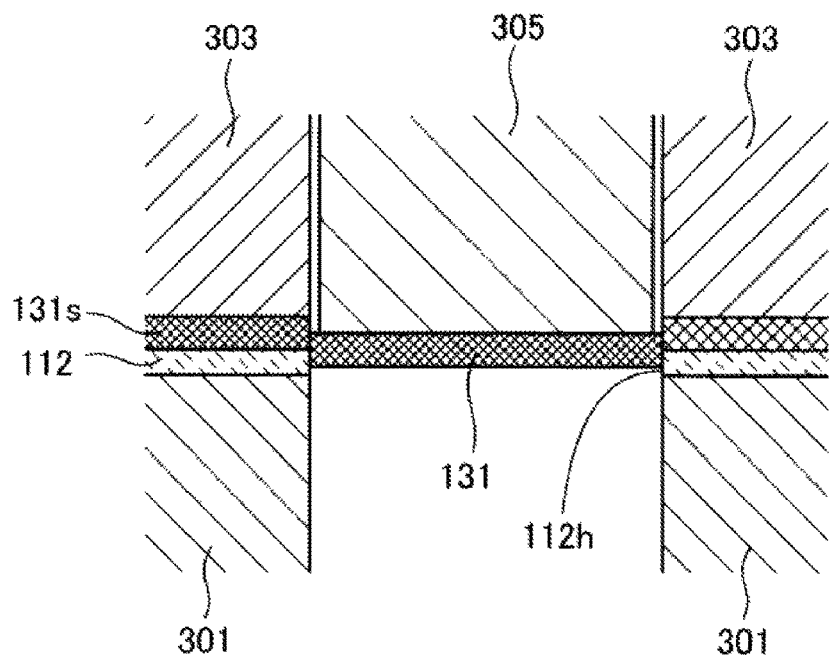
Figure 9:
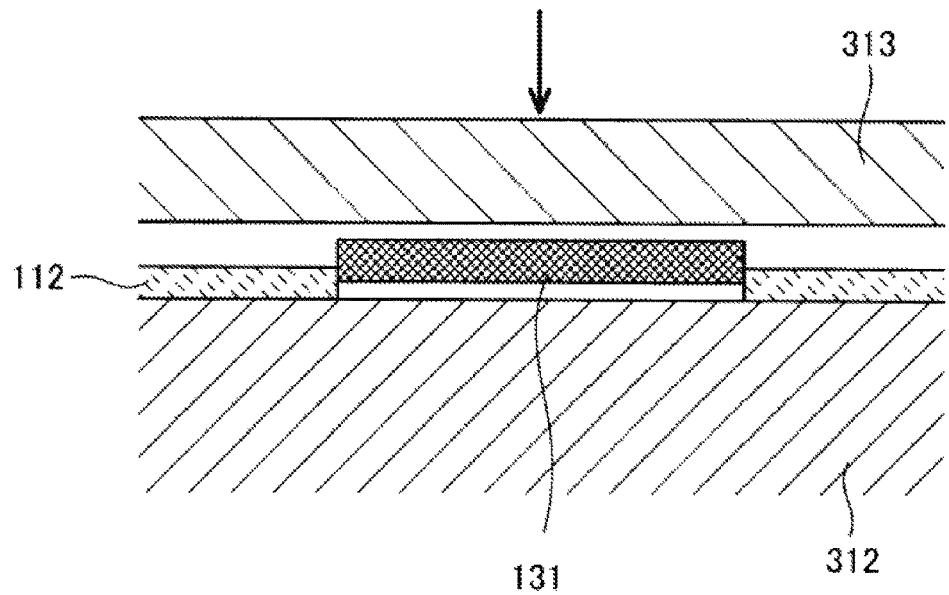
FIG. 9 is a view for explaining a method for compressing a detection insulating portion and a detection electrolyte portion.
Figure 9:
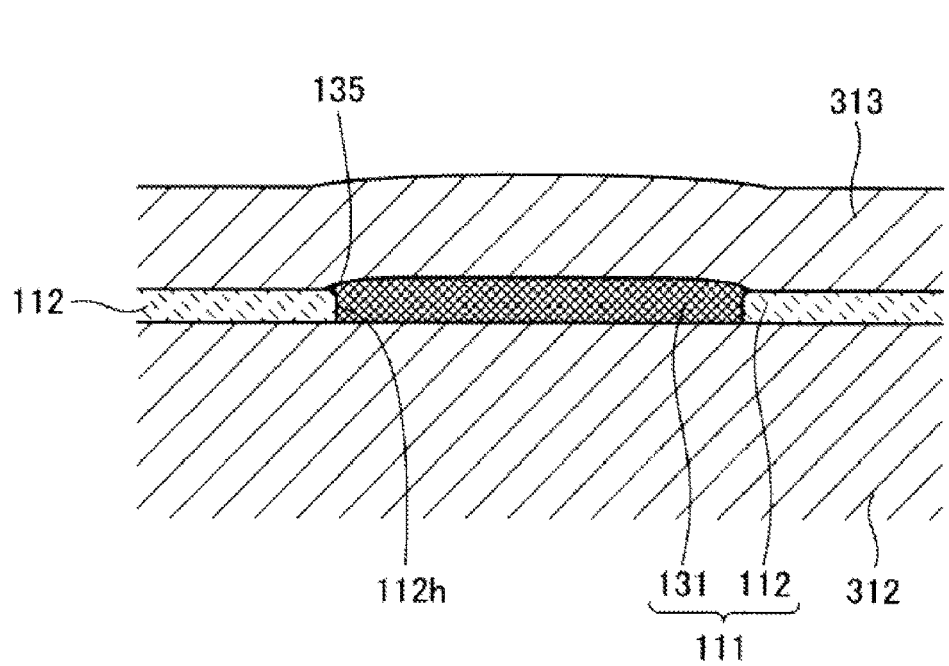

FIG. 7 is a diagram for explaining a method for forming the through-hole 112h in the unsintered insulating-portion sheet 112s. In FIGS. 7 to 9, a direction to the lower side of each figure is a vertically downward direction. In the present embodiment, as shown in FIG. 7(a), first, a lower mold 301 and an upper mold 303, each having a hole having a shape and a size according to the through-hole 112h, are prepared, and the unsintered insulating-portion sheet 112s is placed between the lower mold 301 and the upper mold 303. Then, as shown in FIG. 7(b), a punch 305 is inserted through the holes formed in the lower mold 301 and the upper mold 303, whereby the through-hole 112h is formed in the unsintered insulating-portion sheet 112s. Thus, an unsintered insulating portion 112 is formed.

Subsequently, the unsintered electrolyte portion 131 is inserted into the through-hole 112h formed in the unsintered insulating portion 112 (step S110 in FIG. 6).

FIG. 8 is a diagram for explaining a method for inserting the unsintered electrolyte portion 131 into the through-hole 112h. In the present embodiment, as shown in FIG. 8(a), first, the unsintered insulating portion 112 having the through-hole 112h, and the unsintered electrolyte-portion sheet 131s are overlaid with each other and placed between the lower mold 301 and the upper mold 303. At this time, the unsintered electrolyte-portion sheet 131s is disposed on the side closer to the punch 305. Then, as shown in FIG. 8(b), by using the punch 305, the unsintered electrolyte portion 131 is punched out from the unsintered electrolyte-portion sheet 131s, and the unsintered electrolyte portion 131 is inserted into the through-hole 112h of the unsintered insulating portion 112. At this time, the unsintered electrolyte portion 131 is inserted into the through-hole 112h of the unsintered insulating portion 112 so that the lower surface of the detection electrolyte portion 131 is located at a position between the upper surface and the lower surface of the detection insulating portion 112. By so doing, a part of the detection electrolyte portion 131 protrudes from the through-hole 112*h* of the detection insulating portion 112.

Subsequently, the unsintered insulating portion 112 and the unsintered electrolyte portion 131 are simultaneously compressed in the thickness direction (step S120 in FIG. 6). In step S120, compression is performed as follows. That is, an unsintered extending portion 135 that is overlaid on a first unsintered insulating surface 113 and extends outward from the through-hole 112*h* is formed on a first unsintered electrolyte surface 133 of the unsintered electrolyte portion 131 so that the thickness of the unsintered extending portion 135 is decreased toward the outer periphery of the unsintered extending portion 135, and the outer periphery of the unsintered extending portion 135 and the first unsintered insulating surface 113 are continuously connected to each other, and a first unsintered extending surface 136 which is a surface, on one side, of the unsintered extending portion 135 continuously connects the first unsintered insulating surface 113 and the first unsintered electrolyte surface 133.

FIG. 9 is a diagram for explaining a method for simultaneously compressing the unsintered insulating portion 112 and the unsintered electrolyte portion 131. In the present embodiment, as shown in FIG. 9(*a*), first, the unsintered insulating portion 112 into which the unsintered electrolyte portion 131 is inserted is disposed on a lower iron plate 312 so that the direction in which the unsintered electrolyte portion 131 protrudes is the vertically upward direction. Then, an upper iron plate 313 thinner than the lower iron plate 312 is pressed against the unsintered insulating portion 112 and the unsintered electrolyte portion 131 simultaneously from the vertical upper side, and a pressure (e.g., 40 kg/cm$^2$) is uniformly applied onto the upper iron plate 313. Then, due to the difference in thickness between the unsintered insulating portion 112 and the unsintered electrolyte portion 131, the thinner upper iron plate 313 curves. However, since the upper iron plate 313 presses the unsintered insulating portion 112 and the unsintered electrolyte portion 131 simultaneously, the upper surface (the first electrolyte surface 133) of the unsintered electrolyte portion 131 and the upper surface (first insulating surface 113) of the unsintered insulating portion 112 are continuously connected, and the extending portion 135 as shown in FIG. 4 is formed at the boundary between the unsintered electrolyte portion 131 and the unsintered insulating portion 112, and the upper corner portion of the through-hole 112*h* has an arc shape. Through the above-mentioned steps, the unsintered detection composite ceramic layer 111 including the unsintered electrolyte portion 131 and the unsintered insulating portion 112 is completed. The unsintered detection composite ceramic layer 111 that has been compressed by the method shown in FIG. 9 is turned upside down and stacked in the order shown in FIG. 4.

The above-mentioned compression process in step S120 shown in FIG. 6 is preferably performed at a temperature not lower than 60° C., and more preferably, at a temperature not lower than 80° C. but not higher than 100° C. By performing the compression under such temperature environment, the unsintered insulating portion 112 and the unsintered electrolyte portion 131 are softened, whereby the upper surface of the unsintered electrolyte portion 131 and the upper surface of the unsintered insulating portion 112 are smoothly connected, and the extending portion 135 can be easily formed.

When the compression process has ended, formation of the conductor layers is performed (step S130 in FIG. 6). Specifically, an unsintered first conductor layer 150 (an unsintered first electrode portion 151 and an unsintered first lead portion 152) is formed by screen printing so as to extend over the first electrolyte surface 133 (refer to FIG. 4) of the unsintered electrolyte portion 131 and the first insulating surface 113 of the unsintered insulating portion 112. Further, an unsintered second conductor layer 155 (an unsintered second electrode portion 156 and an unsintered second lead portion 157) is formed by screen printing so as to extend over the second insulating surface 114 of the unsintered insulating portion 112 and the second electrolyte surface 134 of the unsintered electrolyte portion 131. Through the above-mentioned steps, the unsintered detection composite ceramic layer 111 is completed. The unsintered pump composite ceramic layer 211 is also completed through the same process steps as described above.

In the gas sensor element 10 of the present embodiment described above, as shown in FIG. 4, the extending portion 135 that is overlaid on the first insulating surface 113 as one surface of the detection insulating portion 112 and extends outward from the through-hole 112*h* is provided at the detection electrolyte portion 131 disposed in the through-hole 112*h* of the detection insulating portion 112. Then, the outer periphery of the extending portion 135 is continuously connected to the first insulating surface 113, and further, the first extending surface 136 as a surface, on one side, of the extending portion 135 continuously connects the first insulating surface 113 and the first electrolyte surface 133. Therefore, it is possible to suppress occurrence of cracking and breaking in the first conductor layer 150 formed over the first insulating surface 113 and the first electrolyte surface 133. Further, generally, the curing shrinkage rate before and after sintering is larger in the detection electrolyte portion 131 than in the detection insulating portion 112. Therefore, by setting the thickness of the detection electrolyte portion 131 to be large, occurrence of a gap between the first conductor layer 150, the detection electrolyte portion 131, and the detection insulating portion 112 can be effectively suppressed.

Further, in the present embodiment, since the extending portion 135 is formed, the opening area of the through-hole 112*h* on the first insulating surface 113 side is increased from the inner side toward the outer side in the thickness direction. Therefore, it is possible to suppress the detection electrolyte portion 131 disposed in the through-hole 112*h* from easily dropping off from the through-hole 112*h* during manufacturing of the gas sensor element 10.

Further, in the present embodiment, the side end portion 137 (refer to FIG. 4), on the first insulating surface 113 side, of the through-hole 112*h* formed in the detection insulating portion 112 has an arc shape that is convex from the inner side to the outer side in the thickness direction of the detection insulating portion 112. Therefore, on the first insulating surface 113 side, an angular corner portion is not formed at the portion where the detection electrolyte portion 131 and the detection insulating portion 112 are overlaid with each other. Therefore, it is possible to alleviate concentration of stress on the boundary between the detection electrolyte portion 131 and the detection insulating portion 112 on the first insulating surface 113 side. Thus, it is possible to suppress occurrence of cracking in the extending portion 135, starting from any point on the boundary between the detection electrolyte portion 131 and the detection insulating portion 112, whereby durability of the gas sensor element 10 can be increased.

Further, in the present embodiment, when the detection insulating portion 112 and the detection electrolyte portion 131 are continuously connected, although the extending portion 135 is formed at the periphery of the detection electrolyte portion 131, the effective area of the through-hole 112*h* formed in the detection insulating portion 112 hardly varies. Therefore, it is possible to suppress variation in the gas detection performance of the gas sensor element 10 due to manufacturing environment or the like.

In the present embodiment, since the pump composite ceramic layer 211 is produced by the same production method as that for the detection composite ceramic layer 111, the same structure as shown in FIG. 4 is produced with respect to the surface, on the one side DT1, of the pump composite ceramic layer 211. Therefore, the first insulating surface 213 of the pump composite ceramic layer 211 and the first electrolyte surface 233 are continuously connected, whereby it is possible to suppress occurrence of cracking and breaking in the first conductor layer 250 of the pump composite ceramic layer 211, disposed on the one side DT1. The structure shown in FIG. 4 may be applied to only one of the detection composite ceramic layer 111 and the pump composite ceramic layer 211. In other words, one of the detection composite ceramic layer 111 and the pump composite ceramic layer 211 may have a structure in which the electrolyte portion and the insulating portion have the same thickness, and the extending portion is not formed.

Furthermore, in the present embodiment, the extending portion 135 is formed on the surface, on the other side DT2, of the detection composite ceramic layer 111. However, an extending portion 435 may be formed on the surface, on the one side DT1, of the detection composite ceramic layer 111. Alternatively, the extending portion 135 may be formed on the surfaces of the detection composite ceramic layer 111 on both the one side DT1 and the other side DT2.

B. Second Embodiment

In the above-described first embodiment, a so-called double-cell type gas sensor element 10 having two composite ceramic layers (the detection composite ceramic layer 111 and the pump composite ceramic layer 211) has been described. However, the structure of the gas sensor element 10 shown in FIG. 4 is also applicable to a so-called single-cell type gas sensor element having one composite ceramic layer.

Figure 10:
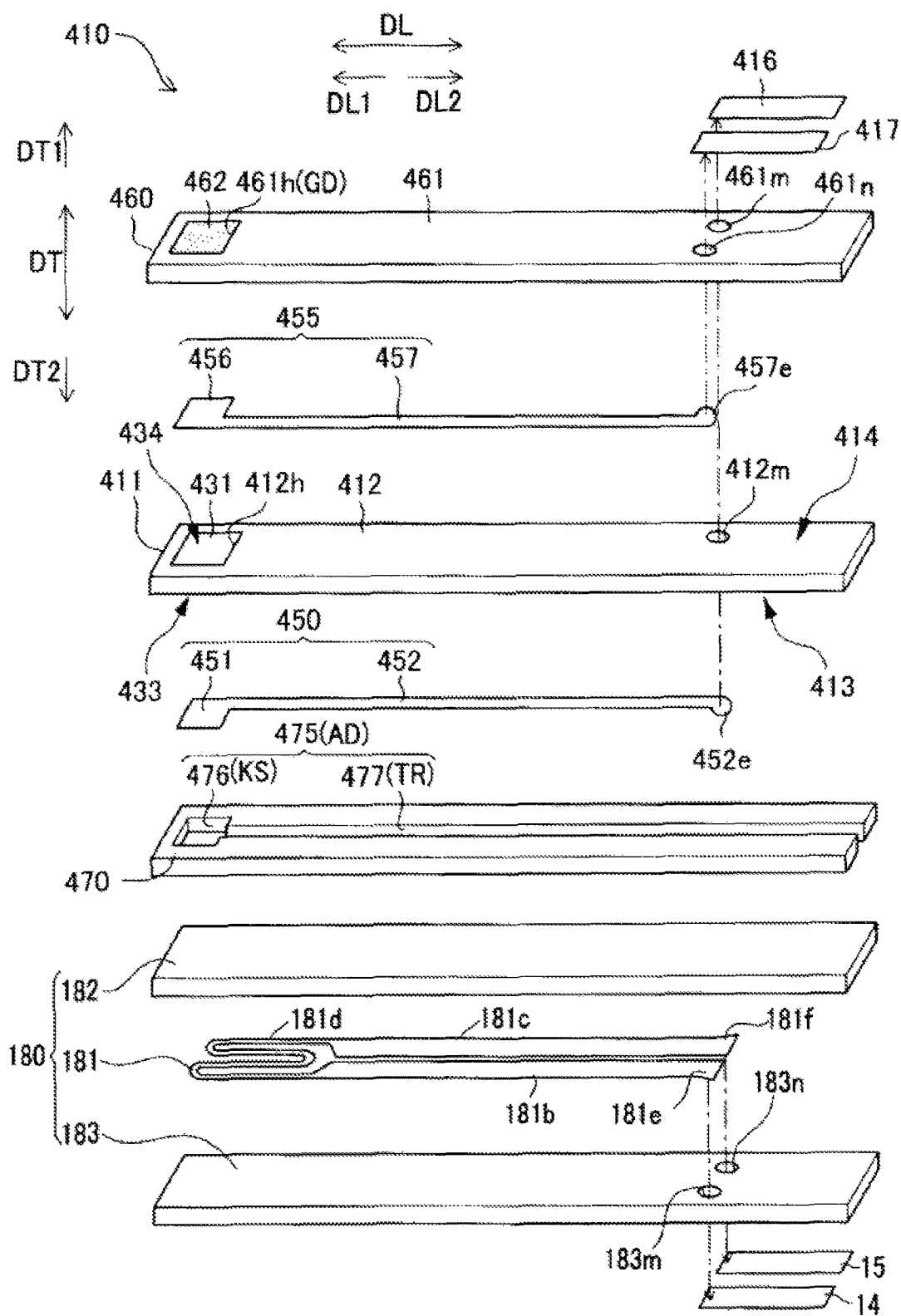
FIG. 10 is an exploded perspective view of a gas sensor element according to a second embodiment.
Figure 11:
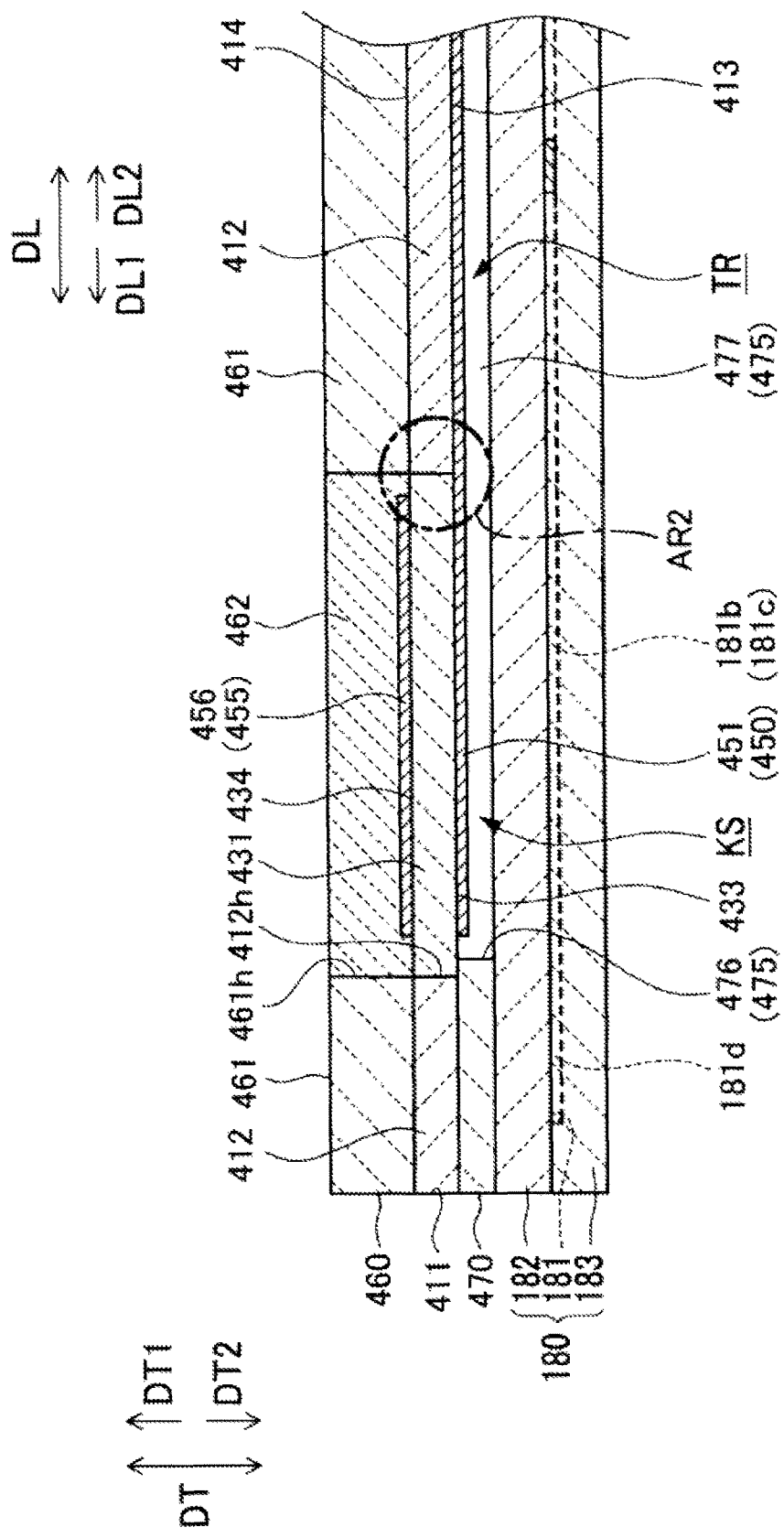
FIG. 11 is a cross-sectional view schematically showing a stacked state of members of the gas sensor element according to the second embodiment.

FIG. 10 is an exploded perspective view of a single-cell type gas sensor element 410. FIG. 11 is a cross-sectional view schematically showing a stacked state of members of the gas sensor element 410. Hereinafter, differences of the structure of the gas sensor element 410 from the gas sensor element 10 according to the first embodiment will be mainly described. In FIG. 10 and FIG. 11, the same members and portions as those of the gas sensor element 10 according to the first embodiment are denoted by the same reference numerals as those in the first embodiment.

The gas sensor element 410 has a composite ceramic layer 411. On the one side DT1 of the composite ceramic layer 411 in the thickness direction, a second conductor layer 455 and a protection layer 460 are stacked in order. On the other side DT2 in the thickness direction of the composite ceramic layer 411, a first conductor layer 450, an introduction passage formation layer 470, and a heater layer 180 are stacked in order.

The composite ceramic layer 411 includes an insulating portion 412 having a through-hole 412*h*, and an electrolyte portion 431. The electrolyte portion 431 is filled in the through-hole 412*h*. The insulating portion 412 has a first insulating surface 413 facing the other side DT2 in the thickness direction, and a second insulating surface 414 facing the one side DT1 in the thickness direction. The electrolyte portion 431 has a first electrolyte surface 433 facing the other side DT2 in the thickness direction, and a second electrolyte surface 434 facing the one side DT1 in the thickness direction.

The first conductor layer 450 is composed of a rectangular first electrode portion 451 formed to be smaller than the opening area of the through-hole 412*h*, and a strip-shaped first lead portion 452 extending from the first electrode portion 451 to the rear side DL2 in the longitudinal direction, which are formed on the first electrolyte surface 433 of the electrolyte portion 431. The first conductor layer 450 is formed extending over the first electrolyte surface 433 and the first insulating surface 413.

The second conductor layer 455 includes a substantially rectangular second electrode portion 456 formed to be smaller than the opening area of the through-hole 412*h*, and a strip-shaped second lead portion 457 extending from the second electrode portion 456 to the rear side DL2 in the longitudinal direction, which are formed on the second electrolyte surface 434 of the electrolyte portion 431.

On the one side DT1 of the composite ceramic layer 411 in the thickness direction, the protection layer 460 is stacked so as to cover the second conductor layer 455. The protection layer 460 includes a porous portion 462 and a protection portion 461. The porous portion 462 is formed of a porous ceramic disposed on the second electrode portion 456 and the electrolyte portion 431 of the composite ceramic layer 411. The protection portion 461 is formed of a dense ceramic that has a through-hole 461*h* penetrating therethrough so as to surround and house the porous portion 462, and is overlaid on the insulating portion 412 of the composite ceramic layer 411 to protect it. The through-hole 461*h* serves as a gas introduction passage GD that introduces the external measurement target gas into the second electrode portion 456.

On the protection portion 461, sensor pad portions 416, 417 are provided. The sensor pad portion 416 electrically communicates with an end portion 452*e*, on the rear side DL2, of the first conductor layer 450 via through-holes 461*m*, 412*m*. The sensor pad portion 417 electrically communicates with an end portion 457*e*, on the rear side DL2, of the second conductor layer 455 via a through-hole 461*n*.

The introduction passage formation layer 470 is made of a dense ceramic, and has an introduction groove 475 penetrating through the introduction passage formation layer 470 in the thickness direction DT. The introduction groove 475 is enclosed by the introduction passage formation layer 470, the composite ceramic layer 411, and the heater layer 180 (insulating layer 182), thereby forming an air introduction passage AD that introduces air into the first electrode portion 451. More specifically, the introduction groove 475 is composed of a reference chamber groove 476 having a rectangular shape in a plan view, and a ventilation groove 477 that is smaller in width than the reference chamber groove 476, extends from the reference chamber groove 476 to the rear side DL2, and is opened at a rear end (right end in FIG. 10) of the introduction passage formation layer 470. The reference chamber groove 476 is enclosed by the introduction passage formation layer 470, the electrolyte portion 431 of the composite ceramic layer 411, and the heater layer 180, thereby forming a reference chamber KS. The ventilation groove 477 is enclosed by the introduction passage formation layer 470, the insulating portion 412 of the composite ceramic layer 411, and the heater layer 180, thereby forming a ventilation passage TR. In the reference chamber KS, the first electrode portion 451 formed on the electrolyte portion 431 is exposed.

The gas sensor element 410 of the present embodiment is disposed on the gas sensor 1 shown in FIG. 1, like the gas sensor element 10 of the first embodiment. However, in the second embodiment, the grommet 73 disposed at the rear end portion of the gas sensor 1 is provided with a filter communicating with the atmosphere. Air is introduced to the ventilation groove 477 of the introduction passage formation layer 470 via the filter. Further, in the present embodiment, the number of the heater pad portions 14, 15 is equal to that in the first embodiment, but the number of the sensor pad portions 416, 417 is two, i.e., one less than that in the first embodiment. Therefore, the number of the terminal members 75, 76 shown in FIG. 1 is four, i.e., one less than that in the first embodiment, and the number of the lead wires 78, 79 is also four, i.e., one less than that in the first embodiment.

In the gas sensor element 410 of the present embodiment, air around the rear end portion of the gas sensor element 410 reaches the first electrode portion 451 through the above-mentioned air introduction passage AD. On the other hand, the measurement target gas around the front end portion of the gas sensor element 410 reaches the second electrode portion 456 through the porous portion 462 disposed in the through-hole 461$h$ of the protection layer 460. Since the electrolyte portion 431 is disposed between the first electrode portion 451 and the second electrode portion 456, when the oxygen concentration of the measurement target gas contacting the second electrode portion 456 is different from the oxygen concentration of air contacting the first electrode portion 451, an oxygen concentration cell is formed by the first electrode portion 451, the electrolyte portion 431, and the second electrode portion 456, and a potential difference is generated between the first electrode portion 451 and the second electrode portion 456. Therefore, the oxygen concentration in the measurement target gas can be detected by obtaining a signal representing this potential difference via the two lead wires 78 electrically communicating with the sensor pad portions 416, 417. When the oxygen concentration is measured, the heater pattern 181 is caused to generate heat by supplying a current to the heater pattern 181 via the two lead wires 79 electrically communicating with the heater pad portions 14, 15, whereby the electrolyte portion 431 is heated and activated.

Figure 12:
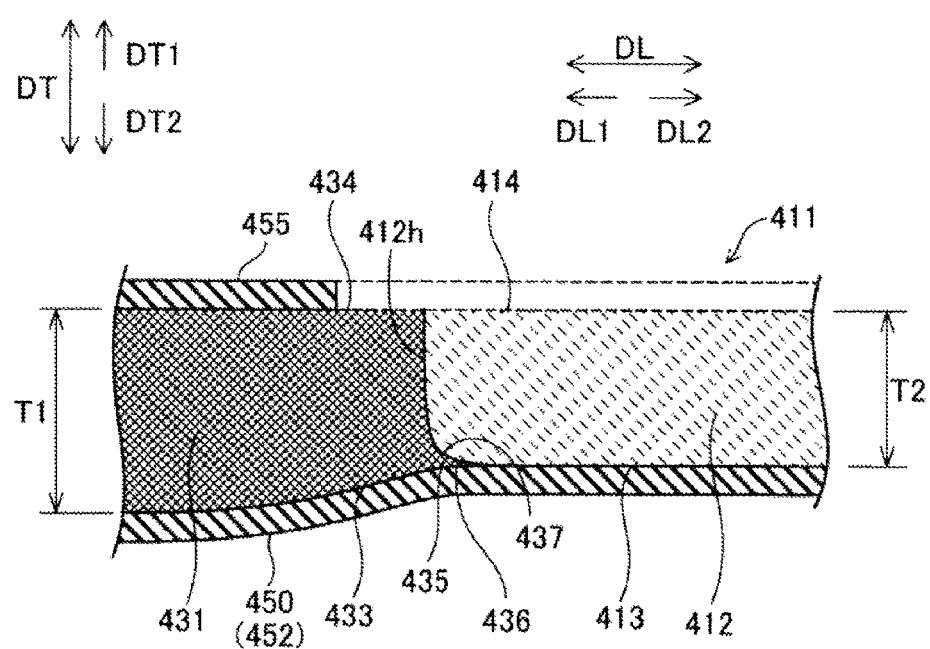
FIG. 12 is an enlarged view of a part around a sectional portion AR2 shown in FIG. 11.

FIG. 12 is an enlarged view of a part of the structure shown in FIG. 11, around a sectional portion AR2. As shown in FIG. 12, the structure of the composite ceramic layer 411 at the position around the boundary between the electrolyte portion 431 and the insulating portion 412 is identical to that of the first embodiment shown in FIG. 4. That is, the thickness T1 of the electrolyte portion 431 is larger than the thickness T2 of the insulating portion 412. The electrolyte portion 431 protrudes toward the first electrolyte surface 433. In addition, the electrolyte portion 431 has, on the first electrolyte surface 433 side, an extending portion 435 that is overlaid on the first insulating surface 413 and extends to the outside of the through-hole 412$h$. The thickness of the extending portion 435 is decreased toward the outer periphery of the extending portion 435. The outer periphery of the extending portion 435 is continuously connected to the first insulating surface 413. Further, a first extending surface 436, which is a surface of the extending portion 435 on the other side DT2, continuously connects the first insulating surface 413 and the first electrolyte surface 433. Therefore, the first insulating surface 413, the first extending surface 436, and the first electrolyte surface 433 are connected so as to form a single plane having no step difference. A side end portion 437, on the first insulating surface 413 side, of the through-hole 412$h$ formed in the insulating portion 412 has an arc shape that is convex from the inner side to the outer side in the thickness direction of the insulating portion 412. That is, the opening area of the through-hole 412$h$ on the first insulating surface 413 side is increased from the inner side toward the outer side in the thickness direction. The structure shown in FIG. 12 is identical over the entire outer periphery of the electrolyte portion 431. Also in the present embodiment, the thickness T1 of the electrolyte portion 431 is the maximum thickness of the electrolyte portion 431. Likewise, the thickness T2 of the insulating portion 412 is the maximum thickness of the insulating portion 412.

Also in the above-mentioned second embodiment, it is possible to suppress occurrence of cracking and breaking in the first conductor layer 450 formed over the first insulating surface 413 and the first electrolyte surface 433. In addition, the same functional effects as those of the first embodiment are achieved. In the second embodiment, the extending portion 435 is formed on the surface, on the other side DT2, of the composite ceramic layer 411. However, the extending portion 435 may be formed on the surface, on the one side DT1, of the composite ceramic layer 411. Alternatively, the extending portion 435 may be formed on the surfaces, on both the one side DT1 and the other side DT2, of the composite ceramic layer 411.

C. Modifications

Modification 1

In the above-mentioned embodiments, the extending portion is formed over the entire periphery of the electrolyte portion of the composite ceramic layer. However, the extending portion may be formed only on a part of the outer periphery of the electrolyte portion, with which the conductor layer is in contact. Also in this structure, it is possible to suppress occurrence of cracking and breaking in the conductor layer.

Modification 2

The gas sensor element can be manufactured not only by the manufacturing method according to the above embodiments but also by various methods. For example, in the above embodiments, the insulating portion and the electrolyte portion are continuously connected by simultaneously pressing a thin iron plate against an unsintered insulating portion and an unsintered electrolyte portion. On the other hand, for example, after inserting an electrolyte portion thicker than an insulating portion into a through-hole of the insulating portion, the same material as the electrolyte portion may be applied so that the electrolyte portion and the insulating portion are continuously connected. Also in this case, the electrolyte portion and the insulating portion can be continuously connected, whereby occurrence of cracking and breaking in the conductor layer can be suppressed.

Modification 3

In the above embodiments, the side end portion, on the first insulating surface side, of the through-hole formed in the insulating portion has an arc shape. However, the side end portion may have a sloped shape or may be formed at a right angle.

The present invention is not limited to the above embodiments and modifications/variations and can be embodied in various forms without departing from the scope of the present invention. For example, it is feasible to appropriately replace or combine any of the technical features of the aspects of the present invention described in "Summary of the Invention" and the technical features of the embodiments and modifications/variations of the present invention in order to solve part or all of the above-mentioned problems or achieve part or all of the above-mentioned effects. Any of these technical features, if not explained as essential in the present specification, may be deleted as appropriate.

DESCRIPTION OF REFERENCE NUMERALS

1: gas sensor
10, 410: gas sensor element
10s: front end portion
10k: rear end portion
14 to 18: pad portion
20: metallic shell
21: ceramic holder
22, 23: powder filler layer
24: ceramic sleeve
25: metal holder
26: crimping packing
27: rear end portion
31: external protector
32: internal protector
31h, 32h: gas introduction hole
51: outer casing
60: separator
62: insertion hole
73: grommet
75, 76: terminal member
78, 79: lead wire
111: detection composite ceramic layer
112: detection insulating portion
112h: through-hole
112m: through-hole
112s: unsintered insulating-portion sheet
113: first insulating surface
114: second insulating surface
131: detection electrolyte portion
131s: unsintered electrolyte-portion sheet
133: first electrolyte surface
134: second electrolyte surface
135: extending portion
136: first extending surface
137: side end portion
150: first conductor layer
151: first electrode layer
152: first lead layer
152e: end portion
155: second conductor layer
156: second electrode layer
157: second lead layer
157e: end portion
160: protection layer
161: protection portion
161h: through-hole
161m, 161n, 161p: through-hole
162: porous portion
170: insulating layer
170h: through-hole
171: body portion
171m, 171p: through-hole
172: porous portion
180: heater layer
181: heater pattern
181b: first lead portion
181c: second lead portion
181d: heat generating portion
181e: end portion
181f: end portion
182, 183: insulating layer
183m, 183n: through-hole
211: pump composite ceramic layer
212: pump insulating portion
212h: through-hole
212m, 212p: through-hole
213: first insulating surface
214: second insulating surface
231: pump electrolyte portion
233: first electrolyte surface
234: second electrolyte surface
250: first conductor layer
251: first electrode layer
252: first lead layer
252e: end portion
255: second conductor layer
256: second electrode layer
257: second lead layer
257e: end portion
301: lower mold
303: upper mold
305: punch
312: lower iron plate
313: upper iron plate
411: composite ceramic layer
412: insulating portion
412h: through-hole
412m, 461m, 461n: through-hole
413: first insulating surface
414: second insulating surface
416, 417: sensor pad portions
431: electrolyte portion
433: first electrolyte surface
434: second electrolyte surface
435: extending portion
436: first extending surface
437: side end portion
450: first conductor layer
451: first electrode portion
452: first lead portion
452e: end portion
455: second conductor layer
456: second electrode portion
457: second lead portion
457e: end portion
460: protection layer
461: protection portion
461h: through-hole
462: porous portion
470: introduction passage formation layer
475: introduction groove
476: reference chamber groove
477: ventilation groove
AX: axis
AR1, AR2: sectional portion
GD: gas introduction passage
AD: air introduction passage
SP: measurement chamber
TR: ventilation passage
KS: reference chamber
DL: longitudinal direction
DL1: front side in longitudinal direction
DL2: rear side in longitudinal direction
DT: thickness direction
DT1: one side in thickness direction
DT2: other side in thickness direction

What is claimed is:

1. A gas sensor element comprising:
a composite ceramic layer including a plate-shaped insulating portion including an insulating ceramic and defining a through-hole in a direction of a thickness of the insulating portion, and an electrolyte portion including a solid electrolyte ceramic and having at least a portion disposed in the through-hole; and
a first conductor layer formed over a first insulating surface as a surface, on one side, of the insulating portion and a first primary electrolyte surface as a surface, on the one side, of the electrolyte portion, wherein
a maximum thickness of the electrolyte portion is larger than a maximum thickness of the insulating portion,
the electrolyte portion has, on a first primary electrolyte surface side, an extending portion that overlays the first insulating surface, extends outside of the through-hole, and protrudes beyond the first insulating surface in the direction of the thickness of the insulating portion,
a thickness of the extending portion decreases toward an outer periphery of the extending portion, and the outer periphery of the extending portion is continuously connected to the first insulating surface, and
a first extending surface as a surface, on the one side, of the extending portion continuously extends between the first insulating surface and the first primary electrolyte surface.

2. The gas sensor element according to claim 1, wherein a side end portion, on the first insulating surface side, of the through-hole defined by the insulating portion has an arc shape that is convex from an inner side toward an outer side in the thickness direction of the insulating portion.

3. A gas sensor comprising a gas sensor element including
a composite ceramic layer including a plate-shaped insulating portion including an insulating ceramic and defining a through-hole in a direction of a thickness of the insulating portion, and an electrolyte portion including a solid electrolyte ceramic and having at least a portion disposed in the through-hole; and
a first conductor layer formed over a first insulating surface as a surface, on one side, of the insulating portion and a first primary electrolyte surface as a surface, on the one side, of the electrolyte portion, wherein
a maximum thickness of the electrolyte portion is larger than a maximum thickness of the insulating portion,
the electrolyte portion has, on a first primary electrolyte surface side, an extending portion that overlays the first insulating surface, extends outside of the through-hole, and protrudes beyond the first insulating surface in the direction of the thickness of the insulating portion,
a thickness of the extending portion decreases toward an outer periphery of the extending portion, and the outer periphery of the extending portion is continuously connected to the first insulating surface, and
a first extending surface as a surface, on the one side, of the extending portion continuously extends between the first insulating surface and the first primary electrolyte surface.

4. The gas sensor element according to claim 3, wherein a side end portion, on the first insulating surface side, of the through-hole defined by the insulating portion has an arc shape that is convex from an inner side toward an outer side in the thickness direction of the insulating portion.

5. A method for manufacturing a gas sensor element including
a composite ceramic layer including a plate-shaped insulating portion including an insulating ceramic and defining a through-hole in a direction of a thickness of the insulating portion, and an electrolyte portion including a solid electrolyte ceramic and having at least a portion disposed in the through-hole; and
a first conductor layer formed over a first insulating surface as a surface, on one side, of the insulating portion and a first primary electrolyte surface as a surface, on the one side, of the electrolyte portion, wherein
a maximum thickness of the electrolyte portion is larger than a maximum thickness of the insulating portion,
the electrolyte portion has, on a first primary electrolyte surface side, an extending portion that overlays the first insulating surface, extends outside of the through-hole, and protrudes beyond the first insulating surface in the direction of the thickness of the insulating portion,
a thickness of the extending portion decreases toward an outer periphery of the extending portion, and the outer periphery of the extending portion is continuously connected to the first insulating surface, and
a first extending surface as a surface, on the one side, of the extending portion continuously extends between the first insulating surface and the first primary electrolyte surface, the method comprising:
(A) a step of inserting, in a through-hole defined by a plate-shaped unsintered insulating portion including the insulating ceramic and with the through-hole in a direction of a thickness of the insulating portion, an unsintered electrolyte portion including the solid electrolyte ceramic, the unsintered electrolyte portion thicker than the unsintered insulating portion;
(B) a step of simultaneously compressing the unsintered insulating portion and the unsintered electrolyte portion in the thickness direction;
(C) a step of forming an unsintered first conductor layer over a first unsintered insulating surface as a surface, on one side, of the unsintered insulating portion and a first primary unsintered electrolyte surface as a surface, on the one side, of the unsintered electrolyte portion; and
(D) a step of sintering the unsintered insulating portion, the unsintered electrolyte portion, and the unsintered first conductor layer to form the composite ceramic layer including the insulating portion the electrolyte portion, and the first conductor layer, wherein
in the step (B), on a first primary unsintered electrolyte surface side of the unsintered electrolyte portion, an unsintered extending portion of the unsintered electrolyte portion which is overlaid on the first unsintered insulating surface and extends outside of the through-hole is formed so as to have a thickness decreasing toward an outer periphery of the unsintered extending portion, and compression is performed such that the outer periphery of the unsintered extending portion and the first unsintered insulating surface are continuously connected to each other and a first unsintered extending surface as a surface, on the one side, of the unsintered extending portion continuously extends between the first unsintered insulating surface and the first primary unsintered electrolyte surface.

* * * * *

UNITED STATES PATENT AND TRADEMARK OFFICE
CERTIFICATE OF CORRECTION

PATENT NO. : 10,247,698 B2
APPLICATION NO. : 14/992577
DATED : April 2, 2019
INVENTOR(S) : Ai Igarashi and Satoshi Okazaki Page 1 of 1

It is certified that error appears in the above-identified patent and that said Letters Patent is hereby corrected as shown below:

In the Claims

Claim 5, Column 18, Line 49, insert --,-- after the term "insulating portion"

Signed and Sealed this
Fourteenth Day of May, 2019

Andrei Iancu
*Director of the United States Patent and Trademark Office*